(12) United States Patent
Weg

(10) Patent No.: US 6,248,789 B1
(45) Date of Patent: *Jun. 19, 2001

(54) ADMINISTRATION OF KETAMINE TO MANAGE PAIN AND TO REDUCE DRUG DEPENDENCY

(76) Inventor: Stuart L. Weg, 498 Island Way, Franklin Lakes, NJ (US) 07417

( * ) Notice: Subject to any disclaimer, the term of this patent is extended or adjusted under 35 U.S.C. 154(b) by 0 days.

This patent is subject to a terminal disclaimer.

(21) Appl. No.: 09/029,146

(22) PCT Filed: Aug. 29, 1996

(86) PCT No.: PCT/US96/14095

§ 371 Date: Feb. 27, 1998

§ 102(e) Date: Feb. 27, 1998

(87) PCT Pub. No.: WO97/07750

PCT Pub. Date: Mar. 6, 1997

(51) Int. Cl.⁷ ................................................. A61K 31/135
(52) U.S. Cl. ..................... 514/647; 424/434; 424/435; 424/436; 424/449
(58) Field of Search .............................. 514/647; 424/434, 424/435, 436, 449

(56) References Cited

U.S. PATENT DOCUMENTS

| | | | |
|---|---|---|---|
| 4,334,526 | 6/1982 | Hamacher | 128/1 R |
| 4,671,953 * | 6/1987 | Stanley et al. | 424/440 |
| 4,921,475 | 5/1990 | Sibalis | 604/20 |
| 5,008,110 | 4/1991 | Benecke et al. | 424/448 |
| 5,087,240 | 2/1992 | Sibalis | 604/20 |
| 5,088,977 | 2/1992 | Sibalis | 604/20 |
| 5,112,804 | 5/1992 | Kowarski | 514/3 |
| 5,132,114 | 7/1992 | Stanley | 424/440 |
| 5,163,899 | 11/1992 | Sibalis | 604/20 |
| 5,164,189 | 11/1992 | Farhadieh et al. | 424/448 |
| 5,254,346 | 10/1993 | Tucker et al. | 424/449 |
| 5,290,561 | 3/1994 | Farhadieh et al. | 424/449 |
| 5,332,213 | 7/1994 | Klose | 273/73 D |
| 5,336,168 | 8/1994 | Sibalis | 604/20 |
| 5,352,456 | 10/1994 | Fallon et al. | 424/448 |
| 5,407,713 | 4/1995 | Wilfong | 428/34.1 |

FOREIGN PATENT DOCUMENTS

| | | |
|---|---|---|
| 1 322 958 | 10/1988 | (CA) . |
| 1096196A | 6/1993 | (CN) . |
| 0 242 643 B1 | 4/1992 | (EP) . |
| WO 91/03236 | 3/1991 | (WO) . |
| WO 93/15737 | 8/1993 | (WO) . |
| WO 95/22965 | 8/1995 | (WO) . |

OTHER PUBLICATIONS

Stedman's Medical Dictionary (1995) Houghton Mifflin Co., p. 812.*
Stanley et al. J. Pain Symptom Manage (7, No. 3), 163–71 (1992) (abstract).*
Tobias, J.D., J. of Intensive Care Medicine, Oct. 6, 294–314 (1995) (Abstract).*
Stedman's Medical Dictionary (Houghton Mifflin Co.), p. 845, 1995.*
Clark et al., Journal of Pain and Symptom Management, 10(4), pp. 310–4 (abstract), 1995.*
J.G. Bovill and J.W. Dundee, "Alterations in Response to Somatic Pain Associated with Anaesthesia", Brit. J. Anaesth. (1971) 43, 496–398.
Matthew A. Howard III, et al., "Intracerebral Drug Delivery in Rats with Lesion–induced Memory Deficits", (1989) J. Neurosurg, 71:105–112.
Robert Langer, "New Methods of Drug Delivery", (1990) Science, 249: 1527–33.
Andre Louon, et al. "Sedation with Nasal Ketamine and Midazolam for Cryotherapy in Retinopathy of Prematurity" (1993) Br. J. Ophthalmol, 77: 529–30.
Oshima et al., "Continous Subcutaneous Injection of Ketamine for Cancer Pain", Can J. Anaesth., (1990) 37:385–6.
Catherine F. Stannard, et al., "Ketamine Hydrochloride in the Treatment of Phantom Limb Pain", (1993) Pain, 54: 227–30.
Jansen (1993) Brit. Med. J. 306: 601–02.
Weksler et al. (1993) Can. J. Anaesthia 40: 119–21.
Adams and Hempelmann (1990) Anaesthesist 39:71–76 (English Abs.).
Reich and Silvay (1989) Can. J. Anaesth. 36: 186–97.
Sadove et al. (1971) Anesth. Analg. 50: 452–57.
Aldrete et al. (1988) Acta Anaesthesiol. Belg. 39 (No. 3 Sup. 2): 95–6.

* cited by examiner

Primary Examiner—Phyllis G. Spivack
(74) Attorney, Agent, or Firm—Darby & Darby

(57) ABSTRACT

The present invention is directed to the transmucosal, transdermal or oral administration of ketamine, either alone or in combination with other pain medications, to manage and treat pain and to reduce drug dependency in a subject.

9 Claims, No Drawings

ADMINISTRATION OF KETAMINE TO MANAGE PAIN AND TO REDUCE DRUG DEPENDENCY

This application is a 35 U.S.C. §371 national phase of PCT/US96/14095, filed Aug. 29, 1996, and claims the priority benefit of provisional application Ser. No. 60/002,946 filed Aug. 30, 1995.

FIELD OF THE INVENTION

The present invention relates to the management of chronic pain without requiring administration of narcotics, or by synergizing with narcotics to allow for a lower effective narcotic dose. The invention also relates to self-management of pain on an outpatient basis.

BACKGROUND OF THE INVENTION

Ketamine ((2-(2-chlorophenyl)-2-(methylamino)-cyclohexanone) is a general anesthetic used by anesthesiologists, veterinarians, and researchers. Usually, ketamine is administered intramuscularly (i.m.) or intravenously (i.v.) for induction of anesthesia. Presently, only ketamine for injection is available for administration (*Physician's Desk Reference*). Nasal administration of ketamine, in one instance with midazolam, for an ophthalmic procedure, and prior to elective surgery in healthy children, has been reported (Louon et al., 1993, Br. J. Ophthalmol. 77:529–530; Weksler et al., 1993, Can. J. Anaesthesia 40:119–121).

Ketamine has also been known to have analgesic properties (Domino et al., 1965, Clin. Pharmacol. Ther. 6:279); analgesia can be achieved with subanesthetic doses of ketamine (Bovill, 1971, Br. J. Anaesth. 43:496; Sadove et al., 1971, Anesth. Analg. 50:452–457). The drug is administered by various routes, including i.v., i.m., caudal, intrathecal, and subcutaneous (s.c.). Subcutaneous administration of ketamine has been used to treat pain following surgery and associated with terminal cancer (see, e.g., Oshima et al., 1990, Can. J. Anaesth. 37:385–386). Ketamine hydrochloride administered via a subcutaneous cannula was reported to successfully treat phantom limb pain (Stannard and Porter, 1993, Pain 54:227–230).

Management of pain, and particularly chronic pain, is complex and frequently unsuccessful. The first line of treatment usually involves administration of $\mu$-opioid agonists, e.g., narcotics such as morphine (see, e.g., Anderson and Brill, 1992, Semin. Anesth. 11:158–171). However, rarely do physicians engage in aggressive pain management. Undertreatment for pain frequently leads to conditions where patients are forced to suffer pain up to the point of tolerability before receiving medication, and the medication is usually only partially effective. Ineffective pain management is a consequence of lack of training, and of fear of narcotics on the part of patients, the medical personnel, and society in general. Children, because of their natural reticence and budding communication skills combined with a greater fear of over-administering "dangerous" narcotics particularly suffer from under treatment for pain.

Moreover, rapid tolerance and marked resistance to narcotics frequently develop, thus rendering these agents ineffective (see, e.g., Abram, 1993, Reg. Anesth. 18(SUPPL):406–413). Non-competitive N-methyl-D-aspartate (NMDA) receptor antagonists, including ketamine, have been reported to interfere with the development of tolerance to the analgesic effects of morphine, possibly through blockade of the NMDA receptor rather than from "side-effects" of the antagonist, since the antagonists were not found to reverse tolerance (Trujillo and Akil, 1994, Brain Res. 633:178–188).

Often, pain management involves administration of a plethora of drugs, such as narcotics, agonist-antagonist agents, butorphanols, benzodiazepines, GABA stimulators, barbiturates, barbiturate-like drugs, orally, e.g., in a pill or liquid formulation, or by i.v. or i.m. injection. Opioid agonists and antagonists may be combined. Thus, a combination of drugs can have offsetting effects. More problematic is the possibility of adverse side effects, particularly gastric distress that accompanies oral administration, or the fear that injections can inspire.

Frequently, a patient suffering from chronic pain will require medication to control stomach and other gastric problems as a result of oral administration of drugs. Alternatives to oral self-administration for most of the analgesic and sedative medications for the treatment of chronic pain are not common, can be cumbersome (e.g., i.v. or s.c. administration requires use of a cannula or needle), and generally require medical training.

U.S. Pat. No. 4,671,953 describes the administration of sedative, analgesic or sedative drugs in a candy matrix, such that the drug enters the bloodstream through the oral mucosal membranes. However, this method suffers from the disadvantage that a sedated patient may fall asleep with the candy remaining in his or her mouth, which can result in choking. Furthermore, because the total dose of the drug in the candy may exceed the desired dose, administration of the candy must be medically supervised. Finally, the candy is simply unsuitable for everyday use, as sucking on a lollipop is an unseemly practice for an employee or business person.

Moreover, when administration is under the control of the patient suffering from pain, i.e., on an outpatient basis, the potential for overdosing or abuse exists, particularly with respect to narcotics.

Thus, there is a need in the art for self-management of pain using non-opioid drugs.

There is a further need in the art for a rapid method for reducing or eliminating breakthrough pain that is refractory to standard treatment regimens.

There is a further need in the art to avoid injection administration of pain medication.

There is a need in the art for a fast, convenient, and socially acceptable method for patient self-administration of medication to manage or control pain.

There is yet a further need in the art to avoid overdose and abuse of self-administered medication, and to enhance the effectiveness of pain medications, particularly narcotic pain medication.

These and other needs in the art have been addressed by the instant invention, which is based on the inventor's discovery that ketamine can surprisingly be administered nasally to alleviate pain safely and effectively, in conjunction with or independently of other pain management regimens.

The citation or identification of any reference in this application shall not be construed as an admission that such reference is available as prior art to the present invention.

SUMMARY OF THE INVENTION

The present invention is broadly directed to a method for treating pain in a subject comprising administering via a transmucosal route a dose of ketamine effective to alleviate pain to a subject suffering from pain. In specific embodiments, administration of ketamine can be via transbuccal, sublingual, vaginal, and rectal routes. Alternatively, the pain-relieving effects of the present invention can be accomplished by administration via oral administration (via the gastrointestinal tract, rather than the oral-pharyngeal mucosa). In a further embodiment, the present invention provides for pulmonary administration of ketamine by inhalation. In a specific aspect, the invention provides an effective pain-relieving dose of ketamine by transdermal administration. Administration of an analgesic dose of ketamine advantageously allows for patient self administration of the drug, which provides for pain management on an outpatient basis. Moreover, ketamine administration via transmucosal and transdermal delivery are generally socially acceptable.

Transmucosal administration of ketamine is rapid, allowing for fast action of the drug. In addition, both transmucosal and transdermal administration are easily accomplished by a non-medically trained patient. The present invention is based, in part, on the discovery that high levels of analgesia can be achieved with small doses of ketamine, particularly ketamine administered by a transmucosal route (e.g., transbuccal, sublingual, vaginal, and rectal), or by a transdermal route. It has further been discovered that effective pain treatment is better achieved by establishing small doses via transdermal or transmucosal delivery, and that these routes of administration avoid side effects associated with a bolus dose of ketamine delivered i.v. or i.m. administration. Furthermore, a small transmucosal or transdermal dose of ketamine can be administered more frequently, which achieves a virtual steady state level of the drug that can be modulated as needed by the subject.

The present invention further advantageously provides for outpatient treatment of episodic and breakthrough pain conditions, which are not amenable to treatment with i.v. or i.m. bolus administration of the drug because of the need for medical intervention for these procedures.

In another embodiment, the present invention contemplates using ketamine synergistically with a traditional pain relief medication, preferably a narcotic pain reliever. Preferably, ketamine can be administered in combination with a lower dose of a second pain relief drug, preferably a narcotic, than would otherwise be indicated for the condition if used alone. As pointed out above, the invention contemplates administration of ketamine transmucosally, more preferably, nasally. In a further embodiment, the present invention provides for pulmonary administration of ketamine by inhalation. Where a patient's condition prevents nasal administration of ketamine, ocular administration, using, e.g., ketamine drops, can be substituted. The invention contemplates transdermal administration as well. In addition to transmucosal administration of ketamine, e.g., nasal, transbuccal, sublingual, vaginal, and rectal, the invention contemplates oral administration (via the gastrointestinal tract, rather than the oral-pharyngeal mucosa), and parenteral administration, e.g., intravenous, intraarterial, intraperitoneal, intradermal, intramuscular, intraventricular, or subcutaneous. In each case, the second pain medication can be administered via the same route as ketamine, where appropriate, or via a different route, e.g., orally while the ketamine is administered transdermally or transbucally.

It has been a surprising discovery in the context of the present invention that ketamine administration to manage pain on top of an ongoing pain management regimen involving other medications, notably narcotics, allows for reduction over time of the other analgesic, particularly a narcotic analgesic. Generally, experience has shown that the effects of different analgesics are additive, and additional analgesics are added to a dosage regimen to supplement it, e.g., when tolerance to a first analgesic builds up.

In this regard, ketamine administration provides the added benefit of reducing drug, particularly narcotic, dependency of individuals who are suffering from a pain condition. In other words, the present invention advantageously provides for treatment of drug dependency developed as a result of medical treatment (rather than drug abuse, for example).

Pain therapy on an outpatient basis advantageously reduces the demands on hospital services, results in a substantial decrease in the cost of treatment, and provides the patient with a more normal living and working environment, which can positively affect treatment outcome. Similarly, reduction in dependency on other pain medications, particularly narcotics, can further reduce the need for medical intervention and the cost of treatment.

Another advantage of the invention is that it avoids or reduces the need to administer narcotic agents for the treatment of chronic pain. Although effective analgesics, narcotics can lose effectiveness due to tolerance or resistance. Narcotics are also highly addictive. In addition, narcotics induce side effects such as nausea, constipation, dizziness, etc., in proportion to dosage. Thus, another advantage of the present invention is that it helps avoid adverse side effects of administration of narcotics.

Yet a further advantage of the invention is that ketamine is an inexpensive, readily available drug, with minor adverse side effects, especially when administered in small doses transmucosally, transdermally, or orally. Thus, the invention contemplates additional savings to the overburdened health care system.

In one aspect, the pain-alleviating dose of ketamine is approximately 0.01 to approximately 1 mg/kg of body weight. In a more preferred aspect, the dose of ketamine is approximately 0.05 to approximately 0.7 mg/kg of body weight. In another embodiment, the total dose of ketamine per nasal administration ranges from about 1 to about 30 mg.

In a specific aspect of the invention, the dose of ketamine is effective to alleviate breakthrough pain in a patient suffering from a chronic pain condition.

In another specific aspect of the invention, the dose of ketamine is effective to alleviate breakthrough pain associated with labor, particularly transition labor.

In another embodiment, which has proved clinically with great success, nasal administration of ketamine is effective for treating migraine headache pain.

In a particular aspect, administration of ketamine can be a supplemental therapy in a pain management regimen that includes administration of one or more of narcotics, analgesics, and sedatives, e.g., as described above.

It should be noted that a further advantage of the instant invention is that it avoids dosing a patient with dysphoric or hallucinogenic amounts of ketamine by providing only an analgesic dose, which is well below the level associated with dysphoria or hallucination. Thus, it avoids the need to administer a dysphoria-suppressive drug, such as a benzodiazepine.

In yet a further embodiment, the present invention contemplates administering a lower dose of a narcotic analgesic than would be effective taken alone to alleviate pain with the ketamine; preferably the narcotic analgesic is administered via the mucosal or transdermal route with the ketamine.

Accordingly, the invention provides various pharmaceutical carriers for patient self-administration of ketamine. Examples of such carriers include, but are not limited to, a suppository, a gum, a candy or lozenge; other carriers include a transbuccal patch and a transdermal patch.

Thus, it is an object of the invention to provide for self administration of a safe, non-narcotic drug for outpatient treatment of pain.

Yet a further object of the invention is to provide a device that can be used outside a hospital or medical office by non-medical personnel for nasal self administration of ketamine.

These and other objects of the present invention will become more readily apparent by reference to the following detailed description.

DETAILED DESCRIPTION OF THE INVENTION

One aspect of the invention provides for transmucosal, transdermal, or oral administration of ketamine for the treatment of pain. In a more preferred aspect, the invention provides a method and device for patient self administration of ketamine for pain management.

The invention can alleviate pain from many causes, including but not limited to shock; limb amputation; severe chemical or thermal burn injury; sprains, ligament tears, fractures, wounds and other tissue injuries; dental surgery, procedures and maladies; labor and delivery; migraine; during physical therapy; post operative pain; radiation poisoning; cancer; acquired immunodeficiency syndrome (AIDS); epidural (or peridural) fibrosis; failed back surgery and failed laminectomy; sciatica; painful sickle cell crisis; arthritis; autoimmune disease; intractable bladder pain; and the like. Mucosal administration of ketamine is also amenable to hospice use, particularly hospices that specialize in the care of cancer and AIDS patients. The present invention is particularly effective for the treatment of intractible pain, whatever its cause.

In one embodiment, transmucosal, transdermal, or oral administration of ketamine can relieve or alleviate episodes of acute breakthrough pain that can occur in a chronic pain condition. In a further embodiment, administration of ketamine via any route can be used as an adjunct therapy to a conventional treatment regimen for a chronic pain condition to alleviate breakthrough pain. In a specific embodiment, infra, nasal (transmucosal) administration of ketamine is effective for treating intractable bladder pain.

A particular advantage of the present invention for reducing labor and delivery pain is that ketamine in low doses is not known to have significant adverse effects on the fetus.

In a related embodiment, transmucosal, transdermal, or oral administration can be used as an adjunct or directly to treat an acute asthma attack. Since unrelated pain conditions can induce asthma, the present invention advantageously provides for alleviating pain, thus blocking the cause of the attack. Furthermore, ketamine (in contrast to narcotic pain medications) is a bronchodilator.

In yet another related embodiment, transmucosal, transdermal, or oral administration of ketamine can be used in the treatment of acute nausea. Rectal or transdermal ketamine is particularly suitable for this condition, as nausea precludes the use of oral medications. In particular, rectal or transdermal ketamine can alleviate pain that may be causing the nausea, and can alleviate the abdominal pain that frequently accompanies sever nausea, without stimulating gag responses or involving oral or nasal passages.

In yet a further related embodiment, transmucosal, transdermal, or oral administration of ketamine can be used to treat acute agitation, for example, agitation exhibited by an alcohol or drug intoxicated individual, or by a person placed under arrest by the police.

Similarly, transmucosal, transdermal, or oral ketamine may be useful in the treatment of shock resulting from severe injuries. Thus, even if a patient fails to sense pain because of severe shock, the extreme pain associated with a severe injury contributes to shock.

The present invention is based on the surprising and unexpected discovery that transmucosal administration of ketamine can alleviate symptoms of chronic pain. Thus, in a specific Example, infra, a patient suffering from intractable bladder pain, and taking a variety of narcotics, analgesics, and sedatives in an unsuccessful attempt to control the pain, was able to achieve more satisfactory pain management by nasal administration of 16–32 mg of ketamine, corresponding to about 0.2–0.6 mg/kg of body weight. (In the specific Example, infra, a dosage of 16–32 mg corresponds to 0.27–0.53 mg/kg of body weight.) The dosage was effective for about 15 minutes to about 1 hour for alleviating pain. The patient was able to reduce the amount of a oral pain medications, which had caused gastric distress.

It has further been found that dozens of patients suffering from intractable pain, migraine headache, chronic fatigue syndrome, or other pain-associated afflictions, have benefitted from the methods and devices of the invention.

Accordingly, the present invention is directed to methods for alleviating chronic or breakthrough pain on an outpatient basis by transmucosal, transdermal, or oral administration of ketamine, and to devices usable by non-medical personnel for transmucosal, transdermal, or oral self-administration of ketamine.

Ketamine will preferably be prepared in a formulation or pharmaceutical composition appropriate for transmucosal, transdermal, or oral administration. Suitable formulations are discussed in detail, infra. In a further embodiment, ketamine can be formulated with a mucosal or dermal penetration enhancer to facilitate delivery of the drug. The formulation can also be prepared with pH optimized for solubility, drug stability, absorption through mucosa or skin, and other considerations.

The invention provides for administration of a therapeutically effective dose of ketamine, i.e., a dose effective to alleviate pain, or to facilitate reduction in dependence on other pain medications, particularly narcotic medications. The actual dose will vary, depending on the body weight of the patient, the severity of the pain, the route of administration, the nature of medications administered concurrently, the number of doses to be administered per day, and other factors generally considered by the ordinary skilled physician in the administration of drugs. In a specific embodiment, the amount of ketamine administered to a patient suffering from chronic pain is about 10% to about 20% of the amount used to induce anesthesia. In another specific embodiment, the dose of ketamine is about 0.01 mg per kg of body weight (0.01 mg/kg) to about 1 mg/kg; preferably about 0.05 mg/kg to about 0.7 mg/kg. In yet another embodiment, the dose ranges from about 1 mg to about 30 mg. Preferably, the effective dose is titrated under the supervision of a physician or medical care provider, so that the optimum dose for the particular application is accurately determined. Thus, the present invention provides a dose suited to each individual patient.

Once the dosage range is established, a further advantage of the invention is that the patient can administer ketamine on an as-needed, dose-to-effect basis. Thus, the frequency of administration is under control of the patient. However, the relatively low dose with each administration will reduce the possibilities for abuse.

Yet another particular advantage of the present invention is that transmucosal, transdermal, or oral administration of ketamine is non-invasive, and provides for introduction into the bloodstream almost as fast as i.v. administration.

More importantly, a patient can control administration of the pain medication, because transmucosal, transdermal, or oral administration provides for precise control over the dosage and effect of the drug used to offset changes in activity and pain levels throughout a day. Transmucosal, transdermal, or oral administration of ketamine optimally provides for dose-to-effect administration of the drug.

Thus, according to the invention, the patient can safely administer an amount of drug effective to alleviate pain by controlling the amount and frequency of administration of a formulation according to the invention. Safe patient regulated control of pain medication is an important advantage because pain is such a subjective condition. The advantage is two-fold here, as the patient can effectively alleviate pain, and the power to alleviate the pain will have significant psychological benefits. A positive psychological attitude can significantly improve the course and outcome of a treatment regimen, as well as making the entire process more bearable to the patient.

Similarly, ketamine, which is not itself addictive, surprisingly acts synergistically with other pain therapies, particularly pain medications, and especially narcotics. Thus, administration of ketamine allows for reduction of the levels of other pain medications, particularly narcotics, with associated savings in cost and avoidance of addiction.

Various terms are used throughout the specification, which are defined herein:

As can be readily appreciated by one of skill in the art, the term "ketamine" refers to ketamine [(2-o-chlorophenyl)-2-(methylamino)-cyclohexanone], pharmaceutically acceptable salts thereof, and biologically equivalent derivatives and analogs thereof, e.g., ketamine aspartate, ketamine succinate, etc. In specific embodiments, ketamine refers to ketamine hydrochloride. Other names for ketamine include ketaject, ketalar, ketanest, ketaset, ketalar, calypos, and feldeross. Also included within the scope of the term "ketamine," as one of ordinary skill would presume, are isomers and enantiomers thereof that demonstrate analgesic properties, e.g., with greater potency or fewer side effects, or both.

The term "mucosal" refers to a tissue comprising a mucous membranes, such as the nasal mucosa pulmonary mucosa, oral-pharyngeal mucosa, stomach and intestines, rectal mucosa, and vaginal mucosa.

The term "transmucosal" in all its grammatical forms refers to administration of a drug through the mucous membrane to the bloodstream for systemic delivery of the drug.

The term "transdermal" in all its grammatical forms refers to administration of a drug through the skin to the bloodstream for systemic delivery of the drug.

The term "oral" refers to administration of a drug through the mouth and into the stomach or intestines, or both.

The advantages of transmucosal, transdermal, and oral administration for drug delivery are that they do not require injection using a syringe and needle, they avoid necrosis that can accompany i.m. administration of drugs, and all three are highly amenable to self administration.

The term "mucosal penetration enhancer" refers to a reagent that increases the rate or facility of transmucosal penetration of ketamine, such as but not limited to, a bile salt, fatty acid, surfactant, or alcohol. In specific embodiments, the permeation enhancer can be sodium cholate, sodium dodecyl sulphate, sodium deoxycholate, taurodeoxycholate, sodium glycocholate, dimethylsulfoxide or ethanol. Suitable penetration enhancers also include glycyrrhetinic acid (U.S. Pat. No. 5,112,804 to Kowarski) and polysorbate-80, the latter preferably in combination with an non-ionic surfactant such as nonoxynol-9, laureth-9, poloxamer-124, octoxynol-9, or lauramide-DEA (European Patent EP 0 242 643 B1 by Stoltz).

A "therapeutically effective amount" of a drug is an amount effective to demonstrate a desired activity of the drug. According to the instant invention, in one embodiment a therapeutically effective amount of ketamine is an amount effective to alleviate, i.e., noticeably reduce, pain in a patient. In another embodiment, a therapeutically effective amount is an amount effective to act synergistically with another pain therapy, e.g., a pain medication such as a narcotic. Preferably the synergistic activity of ketamine co-administration is reflected by reduced dependency on the other pain therapy, particularly a narcotic analgesic, without reducing, and preferably enhancing, the level of pain relief.

As used herein, the term "pharmaceutically acceptable" refers to a biologically or pharmacologically compatible for in vivo use, and preferably means approved by a regulatory agency of the Federal or a state government or listed in the U.S. Pharmacopeia or other generally recognized pharmacopeia for use in animals, and more particularly in humans.

The term "breakthrough pain" is used herein in accordance with its usual meaning in pain treatment. For example, breakthrough pain can refer to pain experienced by a subject receiving treatment for pain, but who experiences a level of pain that is not treatable by the current treatment regimen. "Spike pain" is an acute form of breakthrough pain. Usually medications or therapies for chronic pain do not provide adequate relief for breakthrough pain, either because the maximum pain relief effects of these regimens have been achieved, because of tolerance to medications that has developed, or because the treatment is not fast enough.

A subject in whom administration of ketamine is an effective therapeutic regimen for management of pain, or for synergism with alternative pain therapy is preferably a human, but can be any animal. Thus, as can be readily appreciated by one of ordinary skill in the art, the methods and devices of the present invention are particularly suited to administration of ketamine to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use. For veterinary use, rectal administration or transdermal administration are convenient and allow for minimal aggravation or irritation of the animal.

Transmucosal Administration of Ketamine

As noted above, the present invention is directed inter alia to transmucosal administration of ketamine. Initial studies have demonstrated that nasal administration of ketamine, either via the nasal mucosa or pulmonary inhalation and absorption via pulmonary mucosa, is higly effective for the treatment of pain. Subsequently, it has been discovered that other routes of transmucosal administration of ketamine are also effective for treatment of pain, as set forth above. In particular, it has surprisingly been discovered that transmucosal administration of ketamine allows for effective pharmacokinetics with low doses of the drug, thus avoiding dysphoria or other side effects associated with bolus i.v. or i.m. dosing. Transmucosal ketamine is particularly indicated for breakthrough and spike pain, e.g., as described in greater detail above.

According to the invention, any transmucosal route of administration, including but not limited to rectal, oral, vaginal, buccal, etc. can be employed. In particular, the present invention is directed to the following transmucosal routes of administration. It can be readily appreciated that any of the transmucosal routes of administration may be enhanced by use of a mucosal penetration enhancer, e.g., as described supra. The selection of a particular mucosal penetration enhancer may depend on the characteristics of the specific mucosa. These factors are addressed in greater detail below.

Administration Via Suppositories

In another aspect, ketamine is formulated in a matrix suitable for rectal (or vaginal) insertion, i.e., in a suppository. The invention is not limited to any particular suppository formulation. Indeed, many suppository formulations are known in the art, e.g, as described in *Remington's Pharmaceutical Sciences, Physician's Desk Reference,* and *U.S. Pharmacopeia.*

Administration via suppositories may be preferred in certain situations, e.g., because convention and custom prefers it, or where nasal administration is deemed unacceptable.

Administration Via a Buccal Patch

According to the invention, ketamine can be formulated in a buccal patch for administration via the interior of the cheek. It may be appreciated that a buccal patch constitutes another form of transmucosal administration. The technology for preparing buccal patch formulations is known in the art, e.g., *Remington's Pharmaceutical Sciences*, supra.

Oral-Pharyngeal Administration

In yet another embodiment, ketamine can be formulated for oral-pharyngeal, including sublingual and transbuccal, administration. For example, ketamine can be incorporated in a "candy" matrix, such as that described in U.S. Pat. No. 4,671,953, in a gum base, or a lozenge. In another embodiment, the ketamine can be formulated in a capsule or pill form for sublingual placement.

It is particularly contemplated that ketamine for oral-pharyngeal administration may be formulated with a flavor masking agent or coating. Many flavor masking agents for use with oral pharmaceuticals are known in the art, and can be selected for use with the present invention.

Oral Administration

In still a further embodiment, ketamine can be formulated for oral administration via the stomach and intestinal mucosa. For oral administration, ketamine can be administered in a carrier designed for drug release in either the stomach (an acidic environment), or the intestines, or both. Many capsules, pills, and matrices for oral administration of a drug are known in the art, and can be selected on the basis of compatibility with ketamine, and the desired point and rate of drug release by the ordinary skilled physician. Oral administration of ketamine may require higher dosages than other routes of administration to overcome the effects of first pass metabolism by the liver.

Transdermal Administration

In a further embodiment, as noted above, the present invention is directed to transdermal administration of ketamine. It has been discovered that transdermal administration of ketamine is also effective for treatment of pain, as set forth above, for many of the same reasons transmucosal administration is effective. In particular, it has surprisingly been discovered that transdermal administration of ketamine allows for effective pharmacokinetics with low doses of the drug, thus avoiding dysphoria or other side effects associated with bolus i.v. or i.m. dosing. Transdermal ketamine is particularly indicated for breakthrough and spike pain, e.g., as described in greater detail above.

Various and numerous methods are known in the art for transdermal administration of a drug, e.g., via a transdermal patch. These methods and associated devices provide for control of the rate and quantity of administration of a drug, and some allow for continuous modulation of drug delivery. Transdermal patches are described in, for example, U.S. Pat. No. 5,407,713, issued Apr. 18, 1995 to Rolando et al.; U.S. Pat. No. 5,352,456, issued Oct. 4, 1004 to Fallon et al.; U.S. Pat. No. 5,332,213 issued Aug. 9, 1994 to D'Angelo et al.; U.S. Pat. No. 5,336,168, issued Aug. 9, 1994 to Sibalis; U.S. Pat. No. 5,290,561, issued Mar. 1, 1994 to Farhadieh et al.; U.S. Pat. No. 5,254,346, issued Oct. 19, 1993 to Tucker et al.; U.S. Pat. No. 5,164,189, issued Nov. 17, 1992 to Berger et al.; U.S. Pat. No. 5,163,899, issued Nov. 17, 1992 to Sibalis; U.S. Pat. Nos. 5,088,977 and 5,087,240, both issued Feb. 18, 1992 to Sibalis; U.S. Pat. No. 5,008,110, issued Apr. 16, 1991 to Benecke et al.; and U.S. Pat. No. 4,921,475, issued May 1, 1990 to Sibalis, the disclosure of each of which is incorporated herein by reference in its entirety.

It can be readily appreciated that a transdermal route of administration may be enhanced by use of a dermal penetration enhancer, e.g., such as enhancers described in U.S. Pat. No. 5,164,189 (supra), U.S. Pat. No. 5,008,110 (supra), and U.S. Pat. No. 4,879,119, issued Nov. 7, 1989 to Aruga et al., the disclosure of each of which is incorporated herein by reference in its entirety.

Administration of Ketamine for Synergy with Other Pain Therapy

In addition to the effects of ketamine alone administered via a transmucosal, transdermal, or oral route, which is particularly effective for breakthrough or spike pain conditions, the present invention is directed to administration of ketamine via any route, including parenteral administration in addition to transmucosal, transdermal, and oral administration. Thus, the present invention is not limited to any particular mode or route of administration of ketamine for its synergistic effects with other pain therapies, particularly drug administration, and most particularly, use of narcotic analgesics. Accordingly, where medical necessity or preference dictates, parenteral administration of ketamine can be effected to synergistically treat pain with other pain therapies.

Alternate pain therapies include non-pharmaceutical treatments, such as but not limited to, chiropractic medicine, acupuncture, biofeedback, and other alternative therapies.

Preferably, the synergistic effects of ketamine administration are reflected by reduced dependency on other pain therapies, or by an reduction in the level of pain experienced, or both. This aspect of the invention is based on the surprising discovery that ketamine allows for a reduction over time of narcotic analgesics. Such a reduction over time runs counter to the normal course of pain treatment, where progressively larger doses of analgesics, particularly narcotic analgesics, are required to overcome tolerance.

Usually, combinations of pain medications yield at best additive or supplemental results. Thus, it is a significant advantage of the present invention that it allows for a reduction in the level of a pain medication, without compromising the level of pain relief.

Parenteral administration generally refers to intravenous injection, and also includes, but is not limited to, intra-arteriole, intramuscular, intradermal, subcutaneous, intraperitoneal, intraventricular, and intracranial administration.

In another embodiment, the ketamine can be delivered in a vesicle, in particular a liposome (see Langer, 1990, Science 249:1527–1533; Treat et al., 1989, in *Liposomes in the Therapy of Infectious Disease and Cancer,* Lopez-Berestein and Fidler (eds.), Liss: New York, pp. 353–365; Lopez-Berestein, ibid, pp. 317–327; see generally ibid). To reduce its systemic side effects, this may be a preferred method for introducing ketamine.

In yet another embodiment, ketamine may be delivered in a controlled release system. For example, ketamine may be administered using intravenous infusion, an implantable osmotic pump, a transdermal patch, liposomes, or other modes of sustained release administration. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see *Medical Applications of Con-* trolled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105).

Other controlled release systems are discussed in the review by Langer (1990, Science 249:1527–1533).

The invention can be better understood by referring to the following example, which is provided merely by way of exemplification and is not intended to limit the invention.

EXAMPLE

A female patient, age 40, weighing approximately 60 kg, presented with intractable bladder pain (interstitial ceptitis), which had been diagnosed 4–5 months previously. Pain management in this patient consisted of 100 mg Demoral every 3 hours; Dilaudid 2–4 mg every 4 hours; Dalmane 30 mg per day; Duralgesic patches (fentanyl transdermal patches); bladder washes with Pyridium (phenaropyridine HCl), which is a urinary tract analgesic; and belladonna and opiate suppositories. In addition to the pain medication, the patient took Zanax and Tagamet to alleviate gastric distress, and Compazine (an anti-emetic) to counteract nausea. Gastric distress and nausea in this patient resulted from the pain medication.

Despite the dosages and range of pain medications used by this patient, satisfactory pain management was not achieved.

A diagnostic pre-sacral, or ilio-hypogastric, nerve block was performed on this patient to alleviate the pain. Unfortunately, the effect of the block was temporary, and the block was associated with significant motor weakness. After the block wore off, the patient stated that she was unable to function, as the most mundane activities were exhausting.

Ketamine (10 mg/cc) drip was administered i.v. over one hour, for a total dose of 40 mg ketamine. This resulted in reduction of the pain level by a factor of 2 (from #20 to about #10–12) as subjectively evaluated by the patient. About 1 hour after ketamine infusion was discontinued, the patient reported that the level of pain had increased to about #15, and thereafter rapidly to its previous level. The patient continued to take the other pain medications without effect.

Four days after the ketamine i.v. challenge, a 5 ml bottle containing 100 mg/ml ketamine solution was prepared. A single spray from the bottle delivered approximately ⅙ ml of solution, i.e., 16 mg of ketamine. The patient was instructed to self-administer 1–2 sprays from the bottle for severe pain. The nasal spray bottle was prepared in order to provide sustainable pain medication on an outpatient basis.

The patient has demonstrated remarkable pain management with nasal administration of ketamine. Nasal ketamine has been particularly effective for control of breakthrough pain. The patient has decreased the amount of the other pain medications.

To date, dozens of patients, including subjects suffering from intractable pain, severe migraine headaches, chronic fatigue syndrome, and other painful afflictions, have successfully employed nasal administration of ketamine to treat these problems.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A method for treating pain in a subject comprising incrementally administering transmucosally a dose of about 0.01 mg/kg of body weight to about 1 mg/kg of ketamine effective to alleviate pain in a subject suffering from pain while avoiding dysphoria.

2. The method according to claim 1, wherein the transmucosal route of admininstration is selected from the group consisting of transbuccal, rectal, vaginal, and oral-pharyngeal.

3. A method for treating pain in a subject comprising administering transdermally a dose of ketamine effective to alleviate pain to a subject suffering from pain, wherein transdermal administration consists of absorption of ketamine non-invasively throuoh the skin to the bloodstream for systemic delivery of the ketamine.

4. The method according to claim 3 wherein the dose of ketamine is approximately 0.01 to approximately 1 mg/kg of body weight.

5. A method for treating pain in a subject comprising incrementally administering orally a dose of about 0.01 mg/kg of body weight to about 1 mg/kg of ketamine effective to alleviate pain to a subject suffering from pain while avoiding dysphoria.

6. The method according to claim 1, 4 or 5, wherein the dose of ketamine is approximately 0.05 to approximately 0.7 mg/kg of body weight.

7. The method according to claim 1, 3, or 5 wherein the pain is breakthrough pain.

8. The method according to claims 1, 3 or 5 wherein pain is migraine headache pain.

9. The method according to claims 1, 3 or 5 wherein pain is chronic pain.

* * * * *